United States Patent
Buettelmann et al.

(10) Patent No.: US 7,399,769 B2
(45) Date of Patent: *Jul. 15, 2008

(54) ARYL-ISOXAZOL-4-YL-IMIDAZO[1,5-A]-PYRIDINE DERIVATIVES

(75) Inventors: Bernd Buettelmann, Schopfheim (DE); Jiaqiang Dong, Shatin (HK); Bo Han, Shanghai (CN); Henner Knust, Rheinfelden (DE); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/640,768

(22) Filed: Dec. 18, 2006

(65) Prior Publication Data
US 2007/0191421 A1    Aug. 16, 2007

(30) Foreign Application Priority Data
Dec. 27, 2005   (EP) .................................. 05112988

(51) Int. Cl.
*A61K 31/4353* (2006.01)
*C07D 471/02* (2006.01)

(52) U.S. Cl. ........................ 514/300; 546/112; 546/113; 546/121; 514/277; 514/279; 514/299

(58) Field of Classification Search ................. 546/112, 546/113, 121; 514/277, 279, 299, 300
See application file for complete search history.

(56) References Cited
FOREIGN PATENT DOCUMENTS
WO    WO 01/34603 A2    5/2001
WO    WO 03/044017 A1    5/2003

*Primary Examiner*—Golam M. Shameem
(74) *Attorney, Agent, or Firm*—George W. Johnston; Patricia S. Rocha-Tramaloni; Kimberly J. Prior

(57) ABSTRACT

The present invention is concerned with aryl-isoxazol-4-yl-imidazo[1,5-a]pyridine derivatives of formula

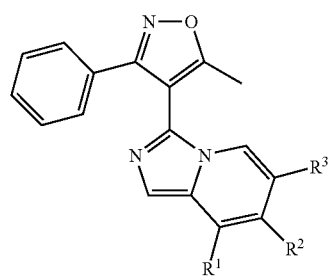

I wherein:
$R^1$, $R^2$, and $R^3$ are as defined herein and pharmaceutically acceptable acid addition salts thereof. These compounds have high affinity and selectivity for GABA A α5 receptor binding sites. The invention also relates to methods for enhancing cognition and treating cognitive disorders like Alzheimer's disease.

14 Claims, No Drawings

ARYL-ISOXAZOL-4-YL-IMIDAZO[1,5-A]-PYRIDINE DERIVATIVES

PRIORITY TO RELATED APPLICATIONS

This application claims the benefit of European Application No. 05112988.0, filed Dec. 27, 2005, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR. It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides aryl-isoxazolo-4-yl-imidazo [1,5-a]pyridine derivatives of formula I:

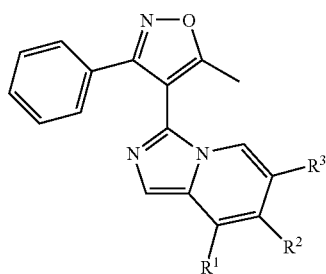

wherein:
R¹ is hydrogen, halogen, hydroxy, lower alkyl, benzyloxy or —O—(CH₂)—(CO)-5 or 6 membered heteroaryl optionally substituted by aryl or lower alkyl;
R² is hydrogen, lower alkyl, or —(CO)—Rᵃ;
R³ is hydrogen, halogen, cyano, lower alkyl, or —(CO)—Rᵃ;
Rᵃ is hydroxy, lower alkoxy, NR'R", wherein R' and R" are each independently hydrogen, cycloalkyl, 5 or 6-membered heterocycloalkyl or is lower alkyl which is optionally substituted by cycloalkyl, cyano, 5 or 6-membered heterocycloalkyl or by 5 or 6-membered heteroaryl; and pharmaceutically acceptable acid addition salts thereof.

The present invention also provides pharmaceutical compositions containing a therapeutically effective amount of a compound of the invention and a pharmaceutically acceptable carrier. The invention further provides processes for preparing the compounds and compositions of the invention.

This class of compounds show high affinity and selectivity for GABA A α5 receptor binding sites and might be useful as a cognitive enhancer or for the treatment of cognitive disorders like Alzheimer's disease. The invention further provides methods of enhancing cognition and treating Alzheimer's disease which comprises administering a therapeutically effective amount of a compound of formula I or a pharmaceutically acceptable salt thereof.

The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-7, preferably from 1-4, carbon atoms, for example, methyl, ethyl, propyl, isopropyl, n-butyl, i-butyl, t-butyl and the like.

The term "lower alkoxy" denotes a lower alkyl group as defined hereinabove, which is linked via an oxygen atom. Examples of lower alkoxy groups are methoxy and ethoxy.

The term "aryl" denotes an unsaturated aromatic carbon ring, for example a phenyl, benzyl or naphthyl group. A preferred aryl group is phenyl.

The term "halogen" denotes chlorine, iodine, fluorine and bromine.

The term "cycloalkyl" denotes a cyclic hydrocarbon ring, having from 3 to 7 carbon ring atoms, for example, cyclopropyl, cyclopentyl or cyclohexyl.

The term "heterocycloalkyl" denotes a saturated 5 or 6 membered ring containing from one to three heteroatoms, such as N, O or S atoms. Examples of such heterocycloalkyl groups are morpholinyl and tetrahydropyranyl as well as those groups which are specifically illustrated by the examples hereinafter.

The term "heteroaryl" denotes an aromatic 5 or 6 membered ring containing from one to three heteroatoms, such as N, O or S atoms. Examples of such aromatic heteroaryl groups are pyridinyl, triazolyl, isoxazolyl, furanyl, thiophenyl, imidazolyl, oxazolyl and pyrazinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides aryl-isoxazolo-4-yl-imidazo [1,5-a] pyridine derivatives of formula I:

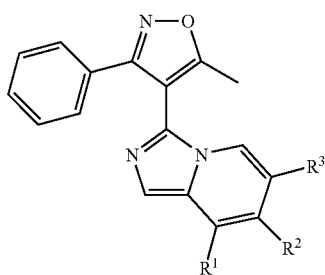

wherein:
$R^1$ is hydrogen, halogen, hydroxy, lower alkyl, benzyloxy or —O—(CH$_2$)—(CO)-5 or 6 membered heteroaryl optionally substituted by aryl or lower alkyl;
$R^2$ is hydrogen, lower alkyl, or —(CO)—$R^a$;
$R^3$ is hydrogen, halogen, cyano, lower alkyl, or —(CO)—$R^a$;
$R^a$ is hydroxy, lower alkoxy, NR'R", wherein R' and R" are each independently hydrogen, cycloalkyl, 5 or 6-membered heterocycloalkyl or is lower alkyl which is optionally substituted by cycloalkyl, cyano, 5 or 6-membered heterocycloalkyl or by 5 or 6-membered heteroaryl; and pharmaceutically acceptable acid addition salts thereof.

Preferred are compounds, which have a binding activity (hKi) of lower than 100 nM and are selective for GABA A α5 subunits and are relatively free of activity at GABA A α1, α2 and α3 receptor binding sites.

As mentioned hereinabove, the compounds of the invention are those compounds of formula I wherein:
$R^1$ is hydrogen, halogen (preferably Cl and Br), hydroxy, lower alkyl (preferably methyl), benzyloxy or —O—(CH$_2$)—(CO)-5 or 6 membered heteroaryl (preferably izoxazolyl) optionally substituted by aryl (preferably phenyl) or lower alkyl (preferably methyl);
$R^2$ is hydrogen, lower alkyl (preferably methyl or ethyl), or —(CO)—$R^a$;
$R^3$ is hydrogen, halogen (preferably Cl or Br), cyano, lower alkyl (preferably methyl or ethyl), or —(CO)—$R^a$;
$R^a$ is hydroxy, lower alkoxy (preferably methoxy or ethoxy), NR'R", wherein R' and R" are each independently hydrogen, cycloalkyl (preferably cyclopropyl), 5 or 6-membered heterocycloalkyl (preferably morpholinyl or tetrahydropyranyl) or lower alkyl optionally substituted by cycloalkyl (preferably cyclopropyl), cyano, 5 or 6-membered heterocycloalkyl (preferably morpholinyl or tetrahydropyranyl) or by 5 or 6-membered heteroaryl (preferably pyridinyl or furanyl);
and pharmaceutically acceptable acid addition salts thereof.

In a certain embodiment of the compounds of formula I of the invention $R^3$ is hydrogen, for example the following compound 3-(5-methyl-3-phenyl-isoxazol-4-yl)-imidazo[1,5-a] pyridine.

In a certain embodiment of the compounds of formula I of the invention $R^3$ is cyano, for example the following compound 3-(5-methyl-3-phenyl-isoxazol-4-yl)-imidazo[1,5-a] pyridine-6-carbonitrile.

In a certain embodiment of the compounds of formula I of the invention $R^3$ is —(CO)—$R^a$, in which $R^a$ is lower alkoxy or NR'R", wherein R' and R" are each independently $R^a$ is hydroxy, lower alkoxy, NR'R", wherein R' and R" are each independently hydrogen, cycloalkyl, 5 or 6-membered heterocycloalkyl or is lower alkyl which is optionally substituted by cycloalkyl, cyano, 5 or 6-membered heterocycloalkyl or by 5 or 6-membered heteroaryl; for example the compound: 3-(5-methyl-3-phenyl-isoxazol-4-yl)-imidazo[1,5-a]pyridine-6-carboxylic acid methyl ester.

In a certain embodiment of the compounds of formula I of the invention $R^1$ is hydrogen.

In a certain embodiment of the compounds of formula I of the invention $R^2$ is hydrogen.

In a certain embodiment of the compounds of formula I of the invention $R^1$ and $R^2$ both are hydrogen.

The present compounds of formula I and their pharmaceutically acceptable salts can be prepared by methods known in the art, for example, by processes described below, which process comprises reacting a compound of formula

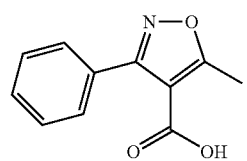

with thionyl chloride to give a compound of formula

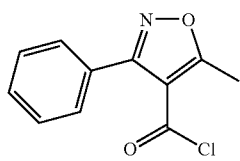

which can then be reacted with a compound of formula IV

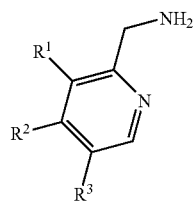

to give a compound of formula V

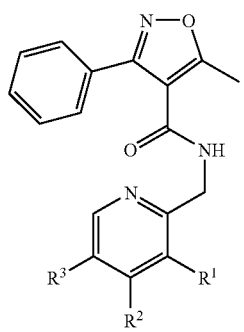

which can then be reacted with a dehydrating reagent such as phosphorous oxychloride in a suitable solvent, such as dichloroethane, to give a compound of formula I

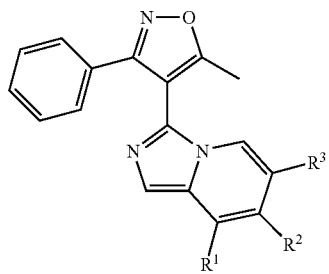

wherein $R^1$, $R^2$ and $R^3$ are as described above,
and, if desired, converting a compound of formula I into a pharmaceutically acceptable salt.

The following schemes describe the processes for preparation of compounds of formula I in more detail.

Scheme 1

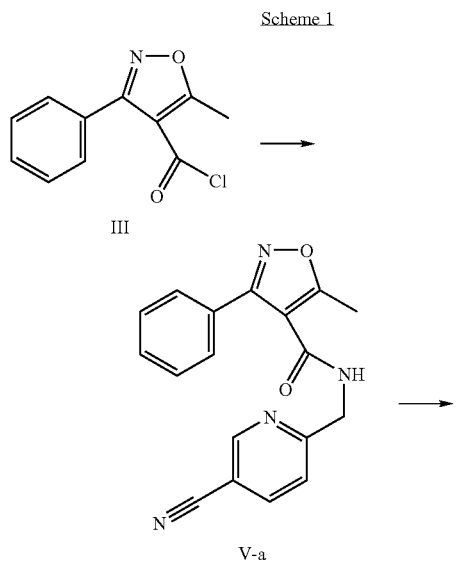

The 5-methyl-3-phenyl-isoxazole-4-carboxylic acid chloride III is treated with 6-aminomethyl-nicotinonitrile hydrochloride salt IV (not shown in scheme I) in a mixture of ethyl acetate and water at 0° C. to give the intermediate amide V-a which can then be heated under reflux with phosphorus oxychloride in dichloroethane to give compound of formula I-a.

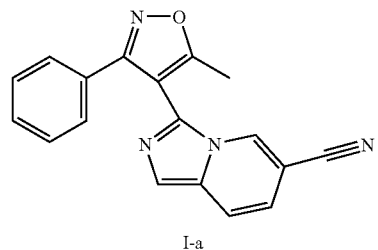

Scheme 2

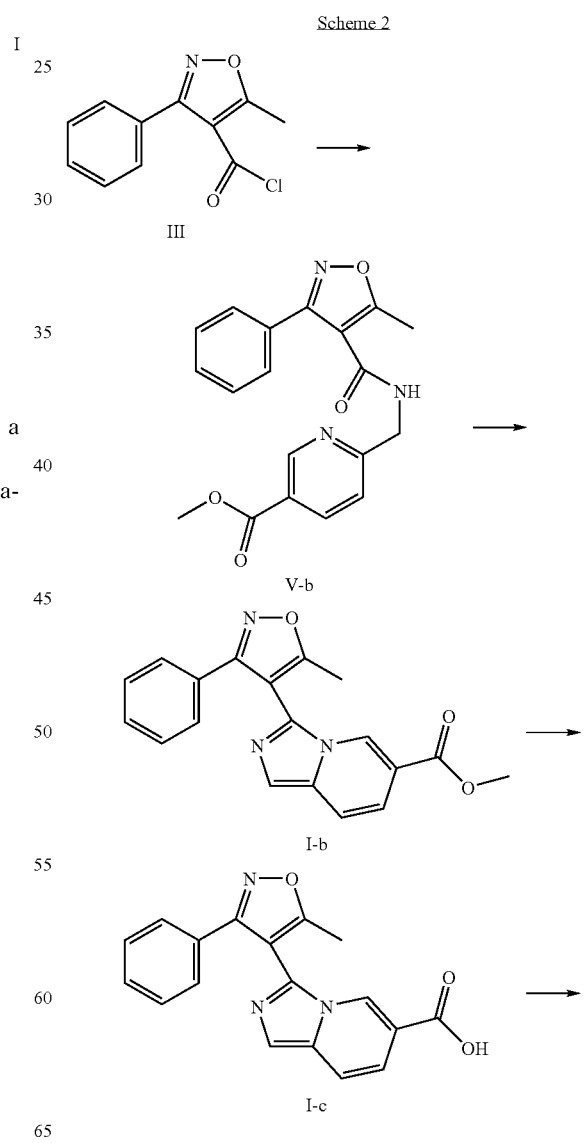

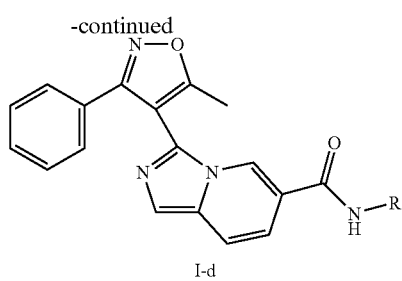

I-d

Alternatively, the 5-methyl-3-phenyl-isoxazole-4-carboxylic acid chloride III can be treated with 6-aminomethyl-nicotinic acid methyl ester IV (not shown in scheme 2) in a mixture of ethyl acetate and water at 0° C. to give the intermediate amide V-b, which can then be heated under reflux with phosphorus oxychloride in dichloroethane to give compound of formula I-b. The ester can then be saponified with lithium hydroxide in a methanol, THF, water mixture to give the acid of formula I-c which can be activated following standard procedures by 1-ethyl-3-(3'-dimethylaminopropyl) carbodiimide, 1-hydroxybenzotriazole, and triethylamine and then reacted with an amine ($RNH_2$) of choice to give compounds of formula I-d.

As mentioned earlier, the compounds of formula I and their pharmaceutically usable salts possess valuable pharmacological properties. The compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of $10-10^{-3 \times 10^{-6}}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from α5 subunits of the rat GABA A receptor of 100 nM or less. In a preferred embodiment the compounds of the invention are binding selective for the α5 subunit relative to the α1, α2 and α3 subunit. The compound of example 1, namely 3-(5-Methyl-3-phenyl-isoxazol-4-yl)-imidazo[1,5-a]pyridine shows a Ki[nM] hα5 value of 77.9 nM.

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragees, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a compound of formula (I) or a pharmaceutically acceptable salt thereof and a therapeutically acceptable carrier are also an object of the present invention, as is a process for the production of such medicaments which comprises bringing one or more compounds of formula (I) or pharmaceutically acceptable salts thereof and, if desired, one or more other therapeutically valuable substances into a galenical dosage form together with one or more therapeutically inert carriers.

Compounds of the invention have high affinity and selectivity for GABA A α5 receptor binding sites. Thus, the invention provides a method of enhancing cognition which comprises administering to an individual a therapeutically effective amount of a compound of formula I or a pharmaceutically acceptable salt thereof. The invention also provides a method for treating Alzheimer's disease which comprises administering to an individual a therapeutically effective amount of a compound of formula I or a pharmaceutically acceptable salt thereof.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Macrocrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-5 are provided for illustration of the invention. They should not be considered as limiting the scope of the invention, but merely as being representative thereof.

EXAMPLE 1

3-(5-Methyl-3-phenyl-isoxazol-4-yl)-imidazo[1,5-a]pyridine a) 5-Methyl-3-phenyl-isoxazole-4-carboxylic acid (pyridin-2-ylmethyl)-amide A mixture of 5-methyl-3-phenyl-isoxazole-4-carboxylic acid (4.06 g, 20 mmol, commercially available) and thionyl chloride (5 mL) was heated under reflux for 3 h. Evaporation of all volatiles afforded 5-methyl-3-phenyl-isoxazole-4-carboxylic acid chloride (4.4 g, 93%) as yellow oil, which was used without further purification in the next reaction. To a mixture of an aqueous solution of 2-picolylamine (0.182 g, 1.68 mmol) in water (2 mL) and ethyl acetate (4 mL) were added sodium hydrogen carbonate (362 mg, 4.2 mmol) in one portion. Then, 5-methyl-3-phenyl-isoxazole-4-carboxylic acid chloride (0.31 g, 1.4 mmol) in ethyl acetate (2 mL) was added dropwise with vigorous stirring under ice-bath cooling keeping the temperature at 0° C. After addition, the reaction mixture was stirred at room temperature for 18 h. The resulting solution was then diluted with ethyl acetate. The organic layer was separated, and the aqueous layer was extracted with ethyl acetate. The combined extracts were then washed with brine, dried over sodium sulphate) and concentrated to afford the title compound (0.38 g, 93%) as a white solid. MS: m/e: 294.1 [M+H]$^+$.

b) 3-(5-Methyl-3-phenyl-isoxazol-4-yl)-imidazo[1,5-a]pyridine

To a solution of 5-methyl-3-phenyl-isoxazole-4-carboxylic acid (pyridin-2-ylmethyl)-amide (0.293 g, 1 mmol) in dichloroethane (5 mL) was added phosphorus oxychloride (0.47 mL, 5 mmol) via a syringe and the resulting mixture heated under reflux overnight. After cooling to room temperature, the mixture was diluted with dichloromethane. Cold saturated sodium bicarbonate (15 mL) was then added slowly and the mixture was vigorously stirred for 15 min. The organic layer was separated and the aqueous was extracted with dichloromethane. The combined extracts were washed with water, dried over sodium sulphate, and evaporated. Purification by preparative HPLC on reversed phase [0.1% aq. ammonia (25%)] afforded the title compound (0.13 g, 47%) as an orange solid. MS: m/e: 276.1 [M+H]$^+$.

EXAMPLE 2

3-(5-Methyl-3-phenyl-isoxazol-4-yl)-imidazo[1,5-a]pyridine-6-carbonitrile a) 5-Methyl-3-phenyl-isoxazole-4-carboxylic acid (5-cyano-pyridin-2-ylmethyl)-amide As described for example 1a, 5-methyl-3-phenyl-isoxazole-4-carboxylic acid chloride (0.266 g, 1.2 mmol) was converted, by using 6-aminomethyl-nicotinonitrile hydrochloride salt (0.17 g, 1 mmol) instead of 2-picolylamine, to the title compound (296 mg, 93%) which was obtained as a white solid. MS: m/e: 319.0 [M+H]$^+$.

b) 3-(5-Methyl-3-phenyl-isoxazol-4-yl)-imidazo[1,5-a]pyridine-6-carbonitrile

As described for example 1b, 5-methyl-3-phenyl-isoxazole-4-carboxylic acid (5-cyano-pyridin-2-ylmethyl)- amide (0.12 g, 0.377 mmol) was converted to the title compound (60 m g, 44%) which was obtained as a light-yellow solid. MS: m/e: 301.3 [M+H]$^+$.

EXAMPLE 3

3-(5-Methyl-3-phenyl-isoxazol-4-yl)-imidazo[1,5-a]pyridine-6-carboxylic acid methyl ester a) 6-{[(5-Methyl-3-phenyl-isoxazole-4-carbonyl)-amino]-methyl}-nicotinic acid methyl ester As described for example 1a, 5-methyl-3-phenyl-isoxazole-4-carboxylic acid chloride (0.5 g, 2.26 mmol) was converted, using 6-aminomethyl-nicotinic acid methyl ester (313 mg, 1.88 mmol) (*J. Med. Chem.* 2002, 45, 5005-5022), instead of 2-picolylamine, to the title compound (0.56 g, 85%) which was obtained as a white solid. MS: m/e: 352.0 [M+H]$^+$.

b) 3-(5-Methyl-3-phenyl-isoxazol-4-yl)-imidazo[1,5-a]pyridine-6-carboxylic acid methyl ester As described for example 1b, 6-{[(5-methyl-3-phenyl-isoxazole-4-carbonyl)-amino]-methyl}-nicotinic acid methyl ester (0.56 g, 1.6 mmol) was converted to the title compound (0.266 g, 50%) which was obtained as a yellow solid. MS: m/e: 334.3 [M+H]$^+$.

EXAMPLE 4

3-(5-Methyl-3-phenyl-isoxazol-4-yl)-imidazo[1,5-a]pyridine-6-carboxylic acid cyclopropylmethyl-amide a) 3-(5-Methyl-3-phenyl-isoxazol-4-yl)-imidazo[1,5-a]pyridine-6-carboxylic acid To a suspension of 3-(5-methyl-3-phenyl-isoxazol-4-yl)-imidazo[1,5-a]pyridine-6-carboxylic acid methyl ester (0.25 g, 0.75 mmol) in water (6 mL) and methanol (3 mL) was added lithium hydroxide monohydrate (0.21 g, 5 mmol) in one portion. The reaction mixture was stirred for 4.5 h at room temperature. After evaporation (removal of methanol), the remaining mixture was extracted with diethyl ether. Then the aqueous layer was acidified to pH~5 with aqueous HCl (2N). The light yellow precipitate was collected by filtration and washed with water to afford the title compound (0.2 g, 83%) as light yellow solid. MS: m/e: 320.1 [M+H]$^+$.

b) 3-(5-Methyl-3-phenyl-isoxazol-4-yl)-imidazo[1,5-a]pyridine-6-carboxylic acid cyclopropylmethyl-amide A solution containing 3-(5-methyl-3-phenyl-isoxazol-4-yl)-imidazo[1,5-a]pyridine-6-carboxylic acid (58 mg, 0.18 mmol), 1-ethyl-3-(3'-dimethylaminopropyl)carbodiimide (52 mg, 0.27 mmol), 1-hydroxybenzotriazole (24 mg, 0.18 mmol), triethylamine (60 μL, 0.45 mmol) and cyclopropyl methylamine (20 mg, 0.27 mmol) in DMF (1 mL) was stirred at room temperature overnight. Purification by preparative HPLC on reversed phase (0.1% aqueous ammonia (25%) afforded the title compound (34 mg, 50%) as a light yellow solid. MS: m/e: 373.3 [M+H]$^+$.

EXAMPLE 5

3-(5-Methyl-3-phenyl-isoxazol-4-yl)-imidazo[1,5-a]pyridine-6-carboxylic acid (tetrahydro-pyran-4-yl)-amide As described for example 4b, 3-(5-methyl-3-phenyl-isoxazol-4-yl)-imidazo[1,5-a]pyridine-6-carboxylic acid (58 mg, 0.18 mmol), was converted, using tetrahydropyran-4-ylamine (28 mg, 0.27 mmol) instead of cyclopropyl methylamine, to the title compound (40 mg, 55%) which was obtained as a light yellow solid. MS: m/e (ESI): 403.3 [M+H]$^+$.

The invention claimed is:

1. An aryl-isoxazol-4-yl-imidazo[1,5-a]pyridine derivative of formula I:

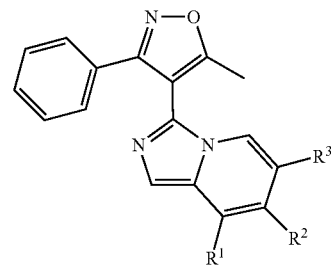

wherein:
R$^1$ is hydrogen, halogen, hydroxy, lower alkyl, benzyloxy or —O—(CH$_2$)—(CO)-5 or 6 membered heteroaryl optionally substituted by aryl or lower alkyl;
R$^2$ is hydrogen, lower alkyl, or —(CO)—R$^a$;
R$^3$ is hydrogen, halogen, cyano, lower alkyl, or —(CO)—R$^a$;
R$^a$ is hydroxy, lower alkoxy, NR'R", wherein R' and R" are each independently hydrogen, cycloalkyl, 5 or 6-membered heterocycloalkyl or is lower alkyl which is optionally substituted by cycloalkyl, cyano, 5 or 6-membered heterocycloalkyl or by 5 or 6-membered heteroaryl; and pharmaceutically acceptable acid addition salts thereof.

2. The compound of claim 1, wherein R$^1$ is hydrogen.
3. The compound of claim 2, wherein R$^2$ is hydrogen.
4. The compound of claim 1, wherein R$^2$ is hydrogen.
5. The compound of claim 1, wherein R$^3$ is hydrogen.
6. The compound of claim 5, which is 3-(5-methyl-3-phenyl-isoxazol-4-yl)-imidazo[1,5-a]pyridine.
7. The compound of claim 1, wherein R$^3$ is cyano.
8. The compound of claim 7, which is 3-(5-methyl-3-phenyl-isoxazol-4-yl)-imidazo[1,5-a]pyridine-6-carbonitrile.
9. The compound of claim 1, wherein R$^3$ is —(CO)—R$^a$, in which R$^a$ is hydroxy, lower alkoxy, NR'R", wherein R' and R" are each independently hydrogen, cycloalkyl, 5 or 6-membered heterocycloalkyl or is lower alkyl which is optionally substituted by cycloalkyl, cyano, 5 or 6-membered heterocycloalkyl or by 5 or 6-membered heteroaryl.
10. The compound of claim 9, which is 3-(5-methyl-3-phenyl-isoxazol-4-yl)-imidazo[1,5-a]pyridine-6-carboxylic acid methyl ester.
11. A pharmaceutical composition comprising a therapeutically effective amount of a compound of formula I

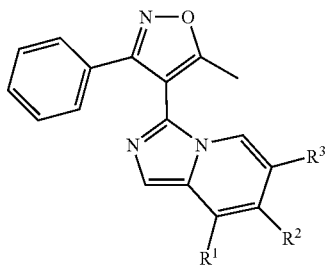

wherein:
R¹ is hydrogen, halogen, hydroxy, lower alkyl, benzyloxy or —O—(CH₂)—(CO)-5 or 6 membered heteroaryl optionally substituted by aryl or lower alkyl;
R² is hydrogen, lower alkyl, or —(CO)—$R^a$;
R³ is hydrogen, halogen, cyano, lower alkyl, or —(CO)—$R^a$;
$R^a$ is hydroxy, lower alkoxy, NR'R", wherein R' and R" are each independently hydrogen, cycloalkyl, 5 or 6-membered heterocycloalkyl or is lower alkyl which is optionally substituted by cycloalkyl, cyano, 5 or 6-membered heterocycloalkyl or by 5 or 6-membered heteroaryl; and pharmaceutically acceptable acid addition salts thereof.

12. The composition of claim 11, wherein the compound is 3-(5-methyl-3-phenyl-isoxazol-4-yl)-imidazo[1,5-a]pyridine.

13. The composition of claim 11, wherein the compound is 3-(5-methyl-3-phenyl-isoxazol-4-yl)-imidazo[1,5-a]pyridine-6-carbonitrile.

14. The composition of claim 11, wherein the compound is 3-(5-methyl-3-phenyl-isoxazol-4-yl)-imidazo[1,5-a]pyridine-6-carboxylic acid methyl ester.

* * * * *